US010578827B2

(12) United States Patent
Cook

(10) Patent No.: US 10,578,827 B2
(45) Date of Patent: Mar. 3, 2020

(54) VARIABLE FOCAL LENGTH LENS SYSTEM WITH QUASI-SINUSOIDAL PERIODIC INTENSITY MODULATED LIGHT

(71) Applicant: Mitutoyo Corporation, Kanagawa-ken (JP)

(72) Inventor: Ted Staton Cook, Kirkland, WA (US)

(73) Assignee: Mitutoyo Corporation, Kanagawa-ken (JP)

( * ) Notice: Subject to any disclaimer, the term of this patent is extended or adjusted under 35 U.S.C. 154(b) by 146 days.

(21) Appl. No.: 15/965,187

(22) Filed: Apr. 27, 2018

(65) Prior Publication Data

US 2019/0331873 A1    Oct. 31, 2019

(51) Int. Cl.
| | |
|---|---|
| H04N 5/232 | (2006.01) |
| G03B 13/00 | (2006.01) |
| G02B 7/04 | (2006.01) |
| H04N 5/235 | (2006.01) |

(52) U.S. Cl.
CPC ............. *G02B 7/04* (2013.01); *H04N 5/2353* (2013.01); *H04N 5/23212* (2013.01)

(58) Field of Classification Search
CPC .. H04N 5/2256; H04N 5/2351; H04N 5/2353; H04N 5/23212; H04N 5/23216; G02F 1/113; G06T 2207/30164; G01N 21/88; G03B 13/32; G03B 13/36; G02B 7/28
See application file for complete search history.

(56) References Cited

U.S. PATENT DOCUMENTS

| | | | |
|---|---|---|---|
| 6,542,180 | B1 | 4/2003 | Wasserman et al. |
| 7,030,351 | B2 | 4/2006 | Wasserman et al. |
| 7,324,682 | B2 | 1/2008 | Wasserman |
| 7,454,053 | B2 | 11/2008 | Bryll et al. |
| 7,570,795 | B2 | 8/2009 | Yu et al. |
| 7,627,162 | B2 | 12/2009 | Blanford et al. |

(Continued)

OTHER PUBLICATIONS

Geis et al., "30 to 50 ns liquid-crystal optical switches," *Optics Express* 18(18):18886-18893, 2010.

(Continued)

*Primary Examiner* — Kelly L Jerabek
(74) *Attorney, Agent, or Firm* — Seed IP Law Group LLP

(57) ABSTRACT

A vision system includes a variable focal length (VFL) lens system, a light source, an exposure time controller and a camera. The VFL lens system includes a tunable acoustic gradient index of refraction (TAG) lens that is controlled to provide a nominally sinusoidal modulation of a focus position. The light source includes a continuous illumination source connected to a source driver that drives the continuous illumination source based on a quasi-sinusoidal periodic drive function to provide corresponding quasi-sinusoidal periodic intensity modulated light. The camera provides a workpiece image based on an image exposure that inputs workpiece image light that arises from illuminating the workpiece with the quasi-sinusoidal periodic intensity modulated light. Utilization of the quasi-sinusoidal periodic intensity modulated light in combination with the nominally sinusoidal focus position modulation results in uniform image exposures and other advantages (e.g., by avoiding over-exposure at the focus extremes of the TAG lens, etc.).

23 Claims, 7 Drawing Sheets

(56) References Cited

U.S. PATENT DOCUMENTS

| | | | |
|---|---|---|---|
| 8,111,905 B2 | 2/2012 | Campbell | |
| 8,111,938 B2 | 2/2012 | Bryll et al. | |
| 9,143,674 B2 | 9/2015 | Gladnick | |
| 2010/0177376 A1* | 7/2010 | Arnold | G02B 3/0087 |
| | | | 359/307 |
| 2011/0133054 A1* | 6/2011 | Campbell | G01B 11/0608 |
| | | | 250/201.2 |
| 2013/0063805 A1* | 3/2013 | Arnold | G02B 3/14 |
| | | | 359/311 |
| 2013/0107002 A1* | 5/2013 | Kikuchi | H04N 5/232 |
| | | | 348/46 |
| 2013/0141782 A1* | 6/2013 | Theriault | G02B 3/14 |
| | | | 359/368 |
| 2014/0368726 A1* | 12/2014 | Gladnick | G01B 11/0608 |
| | | | 348/349 |
| 2015/0145980 A1* | 5/2015 | Bryll | G02B 21/241 |
| | | | 348/79 |
| 2015/0293496 A1 | 10/2015 | Fontecchio | |
| 2017/0013185 A1* | 1/2017 | Gladnick | H04N 5/23212 |
| 2017/0078549 A1 | 3/2017 | Emtman et al. | |
| 2017/0324895 A1* | 11/2017 | Bryll | G01N 21/8806 |
| 2018/0088440 A1* | 3/2018 | Gladnick | G01N 21/8806 |

OTHER PUBLICATIONS

Mermillod-Blondin et al., "High-speed varifocal imaging with a tunable acoustic gradient index of refraction lens," *Optics Letters* 33(18):2146-2148, 2008.

Mitutoyo Corporation & Micro Encoder Inc., "QVPAK 3D CNC Vision Measuring Machine," User's Guide Version 7, Manual No. 99MCB225A, Series No. 359, Jan. 2003. (329 pages).

\* cited by examiner

VARIABLE FOCAL LENGTH LENS SYSTEM WITH QUASI-SINUSOIDAL PERIODIC INTENSITY MODULATED LIGHT

BACKGROUND

Technical Field

This disclosure relates to precision metrology using a variable focal length (VFL) lens, and more particularly to vision systems (e.g., machine vision inspection systems) in which a high speed VFL lens periodically modulates a focus position.

Description of the Related Art

Various types of vision systems (e.g., precision machine vision inspection systems) may be utilized to obtain precise dimensional measurements of objects and to inspect various other object characteristics, and may include a computer, a camera and optical system, and a precision stage that moves to allow workpiece traversal and inspection. One exemplary prior art system is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the QVPAK 3D CNC Vision Measuring Machine User's Guide, published January 2003, which is hereby incorporated by reference in its entirety. This type of system uses a microscope-type optical system and moves the stage to provide inspection images of either small or relatively large workpieces.

General-purpose precision machine vision inspection systems are generally programmable to provide automated video inspection. Such systems typically include GUI features and predefined image analysis "video tools" such that operation and programming can be performed by "non-expert" operators. For example, U.S. Pat. No. 6,542,180, which is incorporated herein by reference in its entirety, teaches a vision system that uses automated video inspection including the use of various video tools.

Multi-lens variable focal length (VFL) optical systems may be utilized for observation and precision measurement of surface heights, and may be included in a microscope and/or precision machine vision inspection system, for example as disclosed in U.S. Pat. No. 9,143,674, which is hereby incorporated herein by reference in its entirety. Briefly, a VFL lens is capable of acquiring multiple images at multiple focal lengths, respectively. One type of known VFL lens is a tunable acoustic gradient ("TAG") lens that creates a lensing effect using sound waves in a fluid medium. The sound waves may be created by application of an electrical field at a resonant frequency to a piezoelectric tube surrounding the fluid medium to create a time-varying density and index of refraction profile in the lens's fluid, which modulates its optical power and thereby the focal length or effective focus position of the vision system. A TAG lens may be used to periodically modulate a focus position at a resonant frequency of up to several hundred kHz, i.e., at a high speed. Such a lens may be understood in greater detail by the teachings of the article, "High speed varifocal imaging with a tunable acoustic gradient index of refraction lens" (*Optics Letters*, Vol. 33, No. 18, Sep. 15, 2008), which is hereby incorporated by reference in its entirety. Tunable acoustic gradient index lenses and related controllable signal generators are available, for example, from TAG Optics, Inc., of Princeton, N.J. The Model TL2.B.xxx series lenses, for example, are capable of modulation up to approximately 600 kHz.

While such VFL lenses can change effective focus position at a very high rate, for a given configuration of a vision system, certain undesirable variations (e.g., which may affect the accuracy of certain types of measurements, processing, etc.) may arise depending at least in part on when images are acquired during the periodic modulation of the focus position (e.g., due in part to different rates of change of the focus position during different phases of the periodic modulation, etc.) A vision system that can provide improvements with regard to such issues would be desirable.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A vision system is provided that includes a variable focal length (VFL) lens system, a light source, an exposure time controller and a camera. The VFL lens system includes a variable focal length tunable acoustic gradient index of refraction (TAG) lens that is controlled to provide a nominally sinusoidal modulation of a focus position of the vision system at a resonant frequency of operation of the TAG lens. The light source includes a continuous illumination source that is configured to provide continuous illumination during a focus position change throughout at least one excursion through an operational focus range of the VFL lens system. The continuous illumination may be utilized to illuminate the workpiece to produce workpiece image light. The continuous illumination source is connected to a source driver that is configured to drive the continuous illumination source based on a quasi-sinusoidal periodic drive function to provide a corresponding quasi-sinusoidal periodic intensity modulated light from the continuous illumination source. The quasi-sinusoidal periodic intensity modulated light is synchronized with the periodic modulation of the nominally sinusoidal focus position modulation such that intensity minima of the quasi-sinusoidal periodic intensity modulated light occur approximately simultaneously with extrema of the nominally sinusoidal focus position modulation.

The exposure time controller is configured to determine an exposure timing and duration that governs an image exposure. The camera is configured to provide a workpiece image based on the image exposure that inputs workpiece image light into the camera that arises from illuminating the workpiece with the quasi-sinusoidal periodic intensity modulated light from the continuous illumination source. The input workpiece image light is transmitted from the workpiece to the camera during the image exposure along an imaging optical path of the VFL lens system that includes the TAG lens.

DETAILED DESCRIPTION

Figure 1:
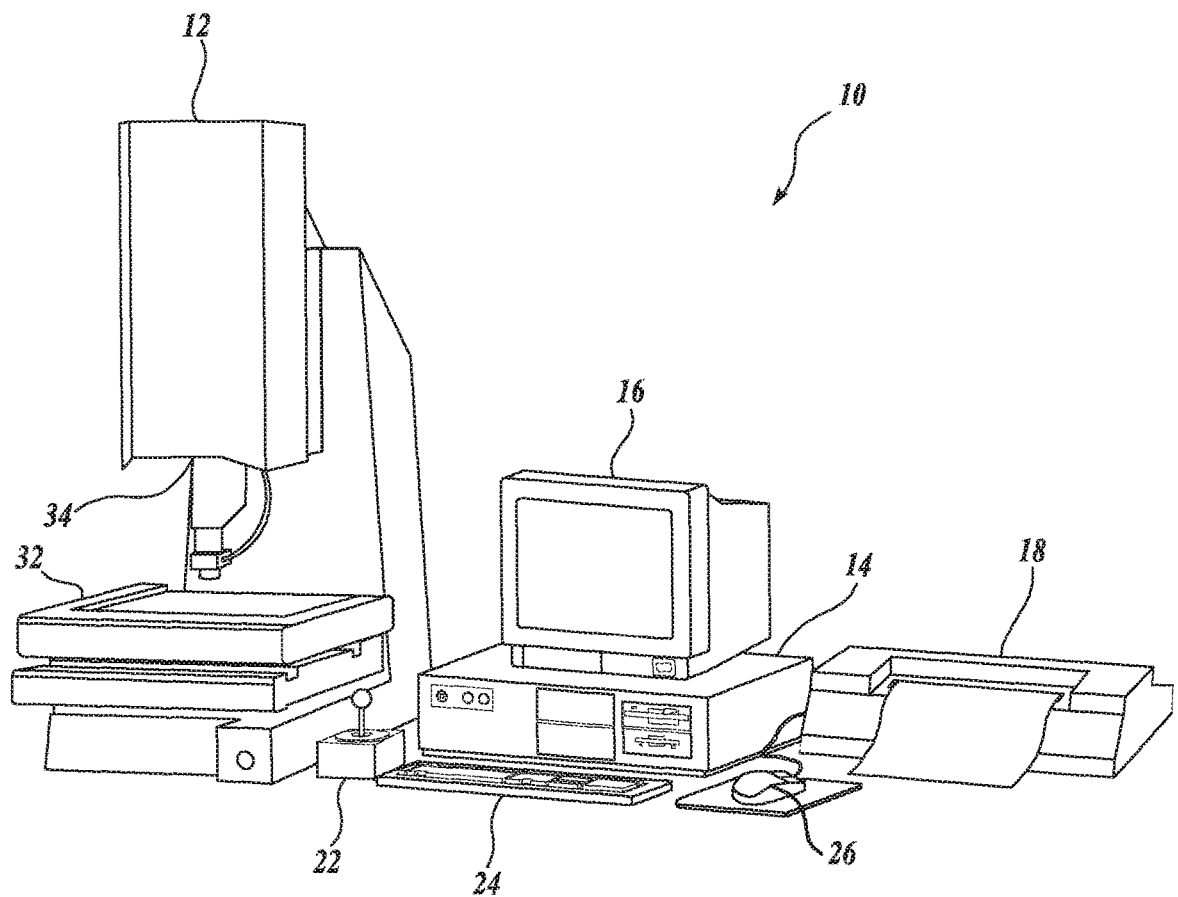
FIG. 1 is a diagram showing various typical components of a general-purpose precision machine vision inspection system.

FIG. 1 is a block diagram of one exemplary implementation of a vision system 10 (e.g., a machine vision inspection system) usable in accordance with principles disclosed herein. The vision system 10 includes a vision measuring machine 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26. The monitor or display 16 may display a user interface suitable for controlling and/or programming the operations of the vision system 10. It will be appreciated that in various implementations, a touchscreen tablet or the like may be substituted for and/or redundantly provide the functions of any or all of the elements 14, 16, 22, 24 and 26.

Those skilled in the art will appreciate that the controlling computer system 14 and/or control system portion 120 of FIG. 2 as described in more detail below may generally be implemented using any suitable computing system or device, including distributed or networked computing environments, and the like. Such computing systems or devices may include one or more general-purpose or special-purpose processors (e.g., non-custom or custom devices) that execute software to perform the functions described herein. Software may be stored in memory, such as random-access memory (RAM), read-only memory (ROM), flash memory, or the like, or a combination of such components. Software may also be stored in one or more storage devices, such as optical-based disks, flash memory devices, or any other type of non-volatile storage medium for storing data. Software may include one or more program modules that include routines, programs, objects, components, data structures, and so on that perform particular tasks or implement particular abstract data types. In distributed computing environments, the functionality of the program modules may be combined or distributed across multiple computing systems or devices and accessed via service calls, either in a wired or wireless configuration.

The vision measuring machine 12 includes a moveable workpiece stage 32 and an optical imaging system 34 that may include a zoom lens or interchangeable objective lenses. The zoom lens or interchangeable objective lenses generally provide various magnifications for the images provided by the optical imaging system 34. Various implementations of the vision system 10 (e.g., as a machine vision inspection system) are also described in commonly assigned U.S. Pat. Nos. 7,454,053; 7,324,682; 8,111,905; and 8,111,938, each of which is hereby incorporated herein by reference in its entirety.

Figure 2:
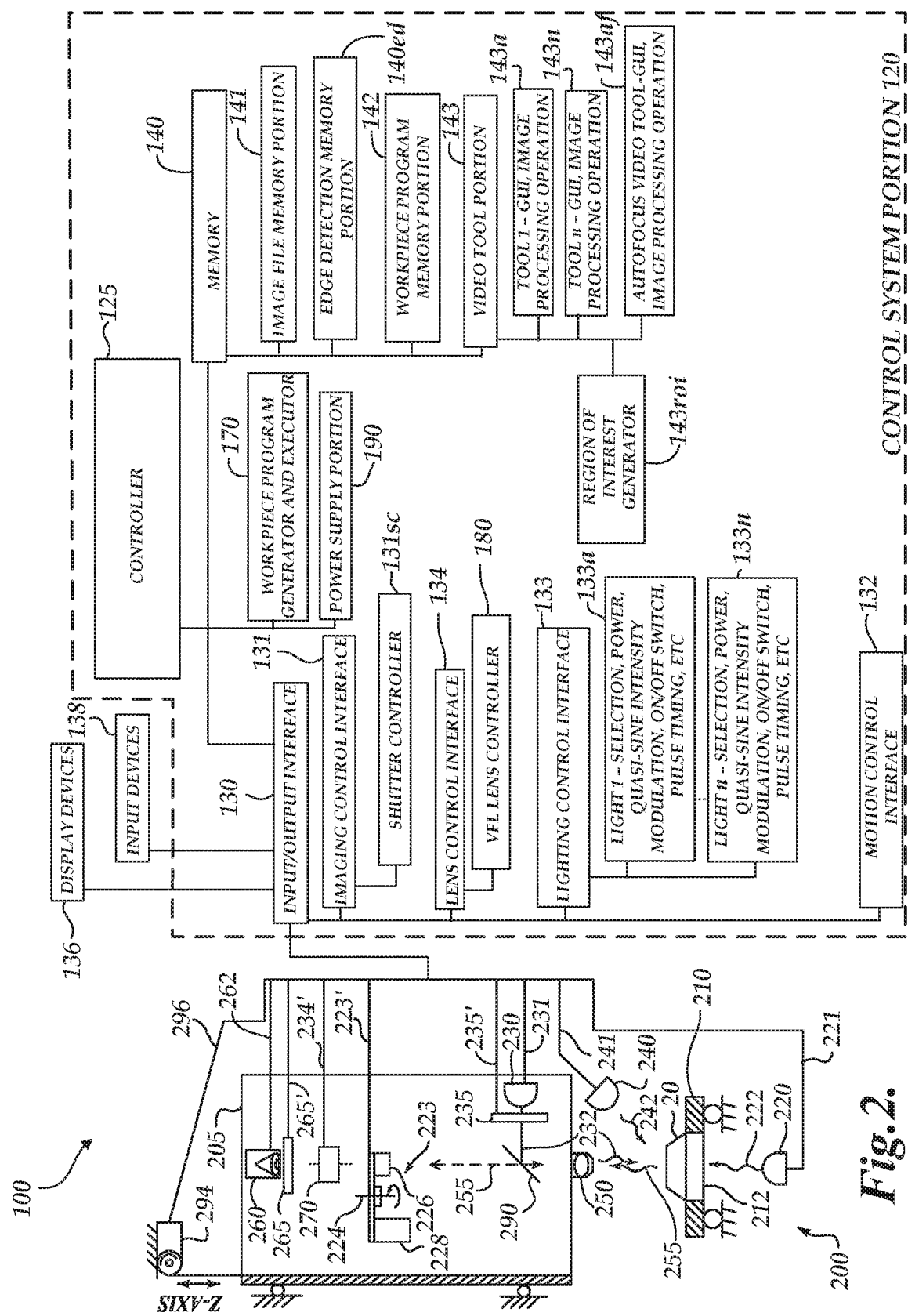
FIG. 2 is a block diagram of a control system portion and a vision components portion of a machine vision inspection system similar to that of FIG. 1 and including certain features disclosed herein.

FIG. 2 is a block diagram of a control system portion 120 and a vision components portion 200 of a vision system 100 similar to the vision system 10 of FIG. 1, including certain features disclosed herein. As will be described in more detail below, the control system portion 120 is utilized to control the vision components portion 200. The vision components portion 200 includes an optical assembly portion 205, light sources 220, 230, 240, and a workpiece stage 210 having a central transparent portion 212. The workpiece stage 210 is controllably movable along x- and y-axes that lie in a plane that is generally parallel to the surface of the stage where a workpiece 20 may be positioned.

The optical assembly portion 205 includes a camera 260, an interchangeable objective lens 250, a variable focal length (VFL) lens 270 (e.g., a TAG lens in various exemplary implementations), and optional light-blocking shutters 235 and 265, as will be described in more detail below. In various implementations, the optical assembly portion 205 may further include a turret lens assembly 223 having lenses 226 and 228. As an alternative to the turret lens assembly, in various implementations a fixed or manually interchangeable magnification-altering lens, or a zoom lens configuration, or the like, may be included. In various implementations, the interchangeable objective lens 250 may be selected from a set of fixed magnification objective lenses that are included as part of the variable magnification lens portion (e.g., a set of objective lenses corresponding to magnifications such as 0.5x, 1x, 2x or 2.5x, 5x, 10x, 20x or 25x, 50x, 100x, etc.)

The optical assembly portion 205 is controllably movable along a z-axis that is generally orthogonal to the x- and y-axes by using a controllable motor 294 that drives an actuator to move the optical assembly portion 205 along the z-axis to change the focus of the image of the workpiece 20. The controllable motor 294 is connected to an input/output interface 130 via a signal line 296. As will be described in more detail below, to change the focus of the image over a smaller range, or as an alternative to moving the optical assembly portion 205, the VFL (TAG) lens 270 may be controlled via a signal line 234' by a lens control interface 134 to periodically modulate the optical power of the VFL lens 270 and thus modulate an effective focus position of the optical assembly portion 205. The lens control interface 134 may include a VFL lens controller 180, as described in more detail below. A workpiece 20 may be placed on the workpiece stage 210. The workpiece stage 210 may be controlled to move relative to the optical assembly portion 205, such that the field of view of the interchangeable objective lens 250 moves between locations on the workpiece 20, and/or among a plurality of workpieces 20.

One or more of a stage light source 220, a coaxial light source 230, and a surface light source 240 (e.g., a ring light) may emit source light 222, 232, and/or 242, respectively, to illuminate the workpiece or workpieces 20. For example, during an image exposure, the coaxial light source 230 may emit source light 232 along a path including a beam splitter 290 (e.g., a partial mirror). As will be described in more detail below, in accordance with various principles disclosed herein, the source light 232 may be quasi-sinusoidal periodic intensity modulated light that is synchronized with the periodic modulation of the nominally sinusoidal focus position modulation of the VFL lens 270.

The source light 232 is reflected or transmitted as workpiece image light 255, and the workpiece image light used for imaging passes through the interchangeable objective lens 250, the turret lens assembly 223 and the VFL lens 270 and is gathered by the camera 260. A workpiece image exposure, which includes the image of the workpiece(s) 20, is captured by the camera 260, and is output on a signal line 262 to the control system portion 120. As will further be described in more detail below, in various implementations different techniques may be utilized for determining an exposure timing and duration that governs the operation of an electronic image integration period provided in the camera to govern the workpiece image exposure.

For example, in various implementations, for controlling the exposure timing and duration, an optional light-blocking shutter 235 may be included and controlled for blocking the source light 232, or an optional light-blocking shutter 265 may be included and controlled for blocking the workpiece image light 255 from reaching the camera 260, and/or the camera 260 may include internal components and/or systems (e.g., an internal and/or integrated light-blocking shutter) for blocking and/or otherwise controlling the amount of workpiece image light 255 that is included in the workpiece image exposure. In various implementations, the camera 260 provides a workpiece image based on the image exposure that inputs workpiece image light 255 into the camera 260 that arises from illuminating the workpiece 20 with the quasi-sinusoidal periodic intensity modulated light 232 from the continuous illumination source 230. As will be described in more detail below with respect to FIG. 3, the input workpiece image light 255 is transmitted from the workpiece 20 to the camera 260 during the image exposure along an imaging optical path OPATH that includes the VFL (TAG) lens 270.

Various light sources (e.g., the light sources 220, 230, 240) may be connected to a lighting control interface 133 of the control system portion 120 through associated signal lines (e.g., the busses 221, 231, 241, respectively). The light-blocking shutters 235 and 265 may be connected to a shutter controller 131sc of the control system portion 120 through associated signal lines (e.g., the busses 235' and 265', respectively). In various implementations, additional light-blocking shutters (e.g., similar to the light-blocking shutter 235) may be included (e.g., for blocking source light from the light sources 220 and/or 240, etc.) In various implementations, the light-blocking shutters 235 and 265 may comprise fast optical switches (e.g., fast liquid crystal optical switches). The control system portion 120 may control the turret lens assembly 223 to rotate along axis 224 to select a turret lens through a signal line or bus 223' to alter an image magnification.

As shown in FIG. 2, in various exemplary implementations, the control system portion 120 includes a controller 125, the input/output interface 130, a memory 140, a workpiece program generator and executor 170, and a power supply portion 190. Each of these components, as well as the additional components described below, may be interconnected by one or more data/control busses and/or application programming interfaces, or by direct connections between the various elements. In various implementations, the control system portion 120 may include and/or otherwise be implemented at least in part by one or more processors (e.g., as part of the controller 125) and a memory (e.g., as part of the memory 140) that is coupled to the one or more processors and stores program instructions that when executed by the one or more processors causes the one or more processors to implement and/or perform at least some of the various functions and elements of the control system portion 120 as described in more detail below.

The input/output interface 130 includes an imaging control interface 131, a motion control interface 132, a lighting control interface 133 and the lens control interface 134. The lens control interface 134 may include or be connected to a VFL lens controller 180 including circuits and/or routines for controlling various image exposures synchronized with the nominally sinusoidal focus position modulation provided by the VFL lens 270. In some implementations, the lens control interface 134 and the VFL lens controller 180 may be merged and/or indistinguishable. In various implementations, the imaging control interface 131 may include an extended depth of field (EDOF) mode (e.g., selectable by a user, etc.) to collect at least one image of a workpiece with a depth of field that is greater than what may be provided by the vision components portion 200 when focused at a single focus position and/or the lens control interface 134 may include an EDOF lens controller (e.g., including a lens focus driving circuit and/or routine, or the like), as described in more detail in U.S. Patent Pub. No. 2017/0078549, which is hereby incorporated herein by reference in its entirety. As described in the '549 publication, in one type of EDOF process, a single image may be exposed along a plurality of focus distances during an exposure time (e.g., utilizing the operation of a VFL lens 270 to achieve the different focus distances during the exposure). The image may be relatively blurry, but may contain image information acquired over the plurality of focus distances. The image may be deconvolved using known or predetermined deconvolution algorithms to obtain a relatively clear image with an extended depth of field.

Figure 3:
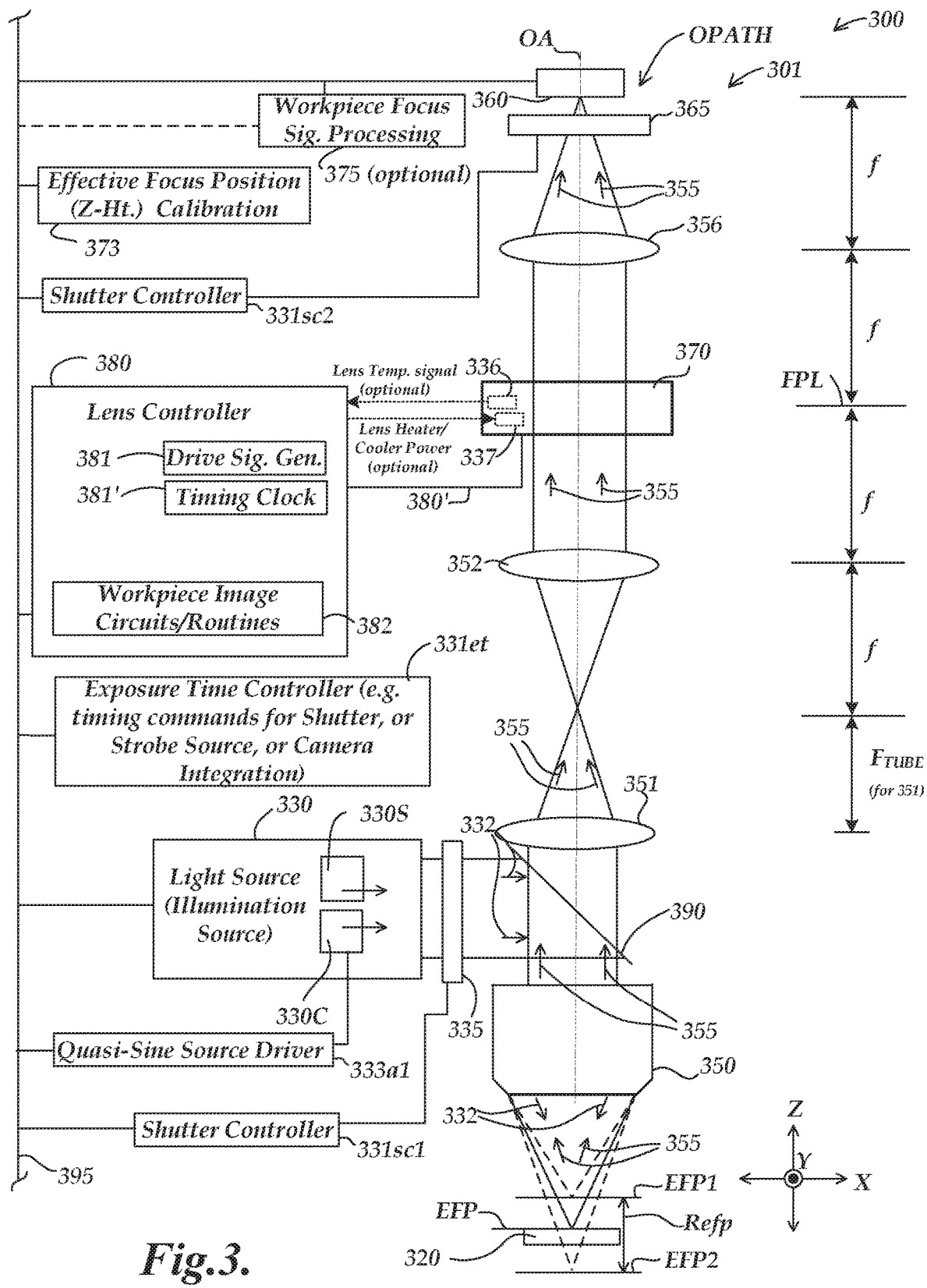
FIG. 3 is a schematic diagram of a VFL lens system adapted to a precision non-contact metrology system such as the machine vision inspection system of FIG. 2, including a continuous illumination source that is driven based on a quasi-sinusoidal periodic drive function according to principles disclosed herein.

In various implementations, the imaging control interface 131 may include the shutter controller 131sc that may consist of one or more shutter controllers for controlling the light-blocking shutters 235 and/or 265 (e.g., providing control signals over the signal lines 235' and 265', respectively). In various implementations, the lighting control interface 133 may include lighting control elements 133a-133n, that control, for example, the selection, power, quasi-sine intensity modulation, on/off switch, pulse timing, etc., if applicable, for the various corresponding light sources of the vision system 100. In some implementations, an exposure time controller 331et as shown in FIG. 3 may provide timing signals and/or control signals to one or more of the shutter controller 131sc, the imaging control interface 131 (e.g., for controlling the camera 260), and/or the lighting control elements 133a-133n, such that they provide an image exposure timing and duration that is synchronized with a desired phase timing of the nominally sinusoidal focus position modulation of the VFL lens, as described in greater detail below. In some implementations, the exposure time controller 331et and one or more of the lighting control elements 133a-133n, shutter controller 131sc and/or imaging control interface 131 may be merged and/or indistinguishable.

The memory 140 may include an image file memory portion 141, an edge-detection memory portion 140ed, a workpiece program memory portion 142 that may include one or more part programs, or the like, and a video tool portion 143. The video tool portion 143 may include a video tool portion 143a and other video tool portions (e.g., 143n) that determine the GUI, image-processing operation, etc., for each of the corresponding video tools, and a region of interest (ROI) generator 143roi that supports automatic, semi-automatic, and/or manual operations that define various ROIs that are operable in various video tools included in the video tool portion 143. Examples of the operations of such video tools for locating edge features and performing other workpiece feature inspection operations are described in more detail in certain of the previously incorporated references, as well as in U.S. Pat. No. 7,627,162, which is hereby incorporated herein by reference in its entirety.

The video tool portion 143 also includes an autofocus video tool 143af that determines the GUI, image-processing operation, etc., for focus height measurement operations. In various implementations, the autofocus video tool 143af may additionally include a high-speed focus height tool that may be utilized to measure focus heights with high speed using hardware described in more detail below with respect to FIG. 3, and as described in more detail in U.S. Pat. No. 9,143,674, which is hereby incorporated herein by reference in its entirety. In various implementations, the high-speed focus height tool may be a special mode of the autofocus video tool 143af that may otherwise operate according to conventional methods for autofocus video tools, or the operations of the autofocus video tool 143af may only include those of the high-speed focus height tool. High-speed autofocus and/or focus position determination for an image region or regions of interest may be based on analyzing the image to determine a corresponding quantitative contrast metric for various regions, according to known methods. For example, such methods are described in U.S. Pat. Nos. 8,111,905; 7,570,795; and 7,030,351, which are hereby incorporated herein by reference in their entirety.

In the context of this disclosure, and as is known by one of ordinary skill in the art, the term "video tool" generally refers to a relatively complex set of automatic or programmed operations that a machine vision user can implement through a relatively simple user interface. For example, a video tool may include a complex pre-programmed set of image-processing operations and computations that are applied and customized in a particular instance by adjusting a few variables or parameters that govern the operations and computations. In addition to the underlying operations and computations, the video tool comprises the user interface that allows the user to adjust those parameters for a particular instance of the video tool. It should be noted that the visible user interface features are sometimes referred to as the video tool, with the underlying operations being included implicitly.

One or more display devices 136 (e.g., the display 16 of FIG. 1) and one or more input devices 138 (e.g., the joystick 22, keyboard 24, and mouse 26 of FIG. 1) may be connected to the input/output interface 130. The display devices 136 and input devices 138 may be used to display a user interface that may include various graphical user interface (GUI) features that are usable to perform inspection operations, and/or to create and/or modify part programs, to view the images captured by the camera 260, and/or to directly control the vision components portion 200.

In various exemplary implementations, when a user utilizes the machine vision inspection system 100 to create a part program for the workpiece 20, the user generates part program instructions by operating the machine vision inspection system 100 in a learn mode to provide a desired image-acquisition training sequence. For example, a training sequence may comprise positioning a particular workpiece feature of a representative workpiece in the field of view (FOV), setting light levels, focusing or autofocusing, acquiring an image, and providing an inspection training sequence applied to the image (e.g., using an instance of one of the video tools on that workpiece feature). The learn mode operates such that the sequence(s) are captured or recorded and converted to corresponding part program instructions. These instructions, when the part program is executed, will cause the machine vision inspection system to reproduce the trained image acquisition and cause inspection operations to automatically inspect that particular workpiece feature (that is the corresponding feature in the corresponding location) on a run mode workpiece, or workpieces, which matches the representative workpiece used when creating the part program. In some implementations, such techniques may be utilized to create a part program instruction for analyzing a workpiece image, as described in more detail in certain of the incorporated references.

FIG. 3 is a schematic diagram of a portion of a vision system 300 similar to the vision system of FIG. 2, including a VFL lens system 301 with a VFL lens 370 (e.g., a TAG lens). In various implementations, the VFL lens system 301 may be adapted to a machine vision system or configured as a standalone system, and may be operated according to principles disclosed herein. It will be appreciated that certain numbered components 3XX of FIG. 3 may correspond to and/or provide similar operations or functions as similarly numbered components 1XX or 2XX of FIG. 2, and may be similarly understood unless otherwise indicated.

As will be described in more detail below, an imaging optical path OPATH comprises various optical components arranged along a path that conveys workpiece imaging light 355 from the workpiece 320 to the camera 360. The imaging light is generally conveyed along the direction of optical axes OA. In the implementation shown in FIG. 3, all the optical axes OA are aligned. However, this implementation is intended to be exemplary only and not limiting. More generally, the imaging optical path OPATH may include mirrors and/or other optical elements, and may take any form that is operational for imaging the workpiece 320 using a camera system (e.g., including the camera 360) according to known principles. In the illustrated implementation, the imaging optical path OPATH includes the VFL lens 370 (which may be included in a 4f imaging configuration) and is utilized at least in part for imaging a surface of a workpiece 320 during a workpiece image exposure.

As shown in FIG. 3, the vision system 300 includes the VFL lens system 301, a light source 330, an exposure time controller 331et, shutter controllers 331sc1 and 331sc2, a quasi-sine source driver 333a1, light-blocking shutters 335 and 365, a camera 360, an effective focus position (Z-height) calibration portion 373, a workpiece focus signal processing portion 375, and a lens controller 380. The VFL lens system 301 includes an objective lens 350, a tube lens 351, a relay lens 352, the VFL lens 370 (e.g., a TAG lens), and a relay lens 356. In various implementations, the various components of the vision system 300 may be interconnected by direct connections or one or more data/control busses (e.g., a system signal and control bus 395) and/or application programming interfaces, etc.

In the implementation shown in FIG. 3, the light source 330 may include a continuous illumination source 330C and a strobe illumination source 330S. In various implementations, the illumination sources 330C and 330S may be merged and/or indistinguishable. As will be described in more detail below, in accordance with principles disclosed herein, the continuous illumination source 330C may be controlled to provide continuous illumination during a focus position change throughout at least one excursion through an operational focus range of the VFL lens system 301, and may be utilized to illuminate the workpiece 320 to produce workpiece image light 355. In various implementations, the continuous illumination source 330C may be connected to a quasi-sine source driver 333a1 that is configured drive the continuous illumination source 330C based on a quasi-sinusoidal periodic drive function to provide a corresponding quasi-sinusoidal periodic intensity modulated light 332. The quasi-sinusoidal periodic intensity modulated light 332 is synchronized with the periodic modulation of the nominally sinusoidal focus position modulation of the VFL lens 370 such that intensity minima of the quasi-sinusoidal periodic intensity modulated light 332 occur approximately simultaneously with extrema of the nominally sinusoidal focus position modulation of the VFL lens 370, as will be described in more detail below with respect to FIGS. 4-6.

In various implementations, the light source 330 may be a "coaxial" or other light source configured to emit the source light 332 (e.g., with continuous illumination and/or strobed illumination from the sources 330C and 330S, respectively) along a path including a beam splitter 390 (e.g., a partially reflecting mirror as part of a beam splitter) and through the objective lens 350 to a surface of a workpiece 320. The objective lens 350 receives the workpiece light 355 that is focused at an effective focus position EFP proximate to the workpiece 320, and outputs the workpiece light 355 to the tube lens 351. The tube lens 351 receives the workpiece light 355 and outputs it to the relay lens 352. In other implementations, analogous light sources may illuminate the field of view in a non-coaxial xial manner. For example, a ring light source may illuminate the field of view. In various implementations, the objective lens 350 may be an interchangeable objective lens and the tube lens 351 may be included as part of a turret lens assembly (e.g., similar to the interchangeable objective lens 250 and the turret lens assembly 223 of FIG. 2). In various implementations, any of the other lenses referenced herein may be formed from or operate in conjunction with individual lenses, compound lenses, etc.

The relay lens 352 receives the workpiece light 355 and outputs it to the VFL (TAG) lens 370. The VFL (TAG) lens 370 receives the workpiece light 355 and outputs it to the relay lens 356. The relay lens 356 receives the workpiece light 355 and outputs it to the camera 360. In various implementations, the camera 360 captures a camera image during an image exposure (e.g., during an integration period of the camera 360) also referred to as an image exposure period, and may provide the corresponding image data to a control system portion. A camera image may include a workpiece image (e.g., of a region of the workpiece 320) provided during a workpiece image exposure. In various implementations, the camera 360 may have a pixel array greater than 1 megapixel (e.g., 1.3 megapixel, with a 1280× 1024 pixel array, with 5.3 microns per pixel).

In the example of FIG. 3, the relay lenses 352 and 356 and the VFL (TAG) lens 370 are designated as being included in a 4f optical configuration, while the relay lens 352 and the tube lens 351 are designated as being included in a Keplerian telescope configuration, and the tube lens 351 and the objective lens 350 are designated as being included in a microscope configuration. All of the illustrated configurations will be understood to be exemplary only, and not limiting with respect to the present disclosure. In various implementations, the illustrated 4f optical configuration permits placing the VFL (TAG) lens 370 (e.g., which may be a low numerical aperture (NA) device) at the Fourier plane of the objective lens 350. This configuration may maintain the telecentricity at the workpiece 320 and may minimize scale change and image distortion (e.g., including providing constant magnification for each Z-height of the workpiece 320 and/or effective focus position EFP). The Keplerian telescope configuration (e.g., including the tube lens 351 and the relay lens 352) may be included between the microscope configuration and the 4f optical configuration, and may be configured to provide a desired size of the projection of the objective lens clear aperture at the location of the VFL (TAG) lens 370, so as to minimize image aberrations, etc.

In various implementations, the lens controller 380 may include a drive signal generator portion 381, a timing clock 381' and workpiece imaging circuits/routines 382. The drive signal generator portion 381 may operate (e.g., in conjunction with the timing clock 381') to provide a periodic drive signal to the high speed VFL (TAG) lens 370 via a signal line 380' (e.g., to provide a nominally sinusoidal modulation of the focus position of the vision system 300 at a resonant frequency of operation of the VFL (TAG) lens). In various implementations, the vision system 300 may comprise a control system (e.g., the control system portion 120 of FIG. 2) that is configurable to operate in conjunction with the lens controller 380 for coordinated operations. In various implementations, the lens controller 380 may generally perform various functions related to imaging a workpiece 320 in a manner synchronized with a desired phase timing of the VFL lens 370, as well as controlling, monitoring and adjusting the driving and response of the VFL lens 370. In various implementations, the workpiece imaging circuits/routines 382 may perform standard workpiece imaging operations for the vision system, synchronized with the phase timing of the VFL lens 370 as is known in the art and as described in certain of the incorporated references.

In various implementations, drift in the operating characteristics of the VFL lens 370 may arise due to unwanted temperature variations. As shown in FIG. 3, the vision system 300 may optionally include a lens heater/cooler 337 associated with the VFL lens 370. The lens heater/cooler 337 may be configured to input an amount of heat energy into the VFL lens 370 and/or perform cooling functions to facilitate heating and/or cooling of the VFL lens 370 according to some implementations and/or operating conditions. In addition, in various implementations a VFL lens monitoring signal may be provided by a temperature sensor 336 associated with the VFL lens 370 to monitor an operating temperature of the VFL lens 370. With respect to the general operations of the VFL lens 370, in various implementations as described above, the lens controller 380 may rapidly adjust or modulate its optical power periodically, to achieve a high-speed VFL lens capable of a periodic modulation (i.e., at a VFL lens resonant frequency) of 250 kHz, or 70 kHz, or 30 kHz, or the like. As shown in FIG. 3, by using the periodic modulation of a signal to drive the VFL lens 370, the effective focus position EFP of the vision system 300 (that is, the focus position in front of the objective lens 350) may be (rapidly) moved within a range Refp (e.g., an autofocus search range). The range Refp may be bound by an effective focus position EFP1 (or EFPmax) corresponding to a maximum optical power of the VFL lens 370 in combination with the objective lens 350, and an effective focus position EFP2 (or EFPmin) corresponding to a maximum negative optical power of the VFL lens 370 in combination with the objective lens 350. In various implementations, the effective focus positions EFP1 and EFP2 may approximately correspond to phase timings of 90 degrees and 270 degrees, respectively, as will be described in more detail below. In various implementations, the middle of the range Refp may be designated as EFPnom, and may correspond to zero optical power of the VFL lens 370 in combination with the nominal optical power of the objective lens 350. According to this description, EFPnom may approximately correspond to the nominal focal length of the objective lens 350 in some implementations.

In one implementation, the optional workpiece focus signal processing portion 375 may input data from the camera 360 and may provide data or signals that are utilized to determine when an imaged surface region (e.g., of the workpiece 320) is at an effective focus position in an image. For example, a group of images acquired by the camera 360 at different Z-heights (e.g., an image stack), may be analyzed using a known "maximum contrast" or "best-focus image" analysis to determine if or when an imaged surface region of the workpiece 320 is at corresponding effective focus position in an image. However, more generally, any other suitable known image focus detection configuration may be used. In any case, the workpiece focus signal processing portion 375 or the like may input an image or images acquired during the periodic modulation of the effective focus position (sweeping of multiple effective focus positions) of the VFL (TAG) lens 370, and determine an image wherein a target feature is best-focused. In some implementations, the workpiece focus signal processing portion 375 may further determine the known phase timing corresponding to that best-focus image and output that "best-focus" phase timing value to the effective focus position calibration portion 373. The effective focus position calibration portion 373 may provide Z-height (effective focus position) calibration data that relates respective Z-heights or effective focus positions to respective "best-focus" phase timings within a period of a standard imaging resonant frequency of the VFL lens 370, wherein the calibration data corresponds to operating the VFL lens 370 according to a standard imaging drive control configuration or reference state.

Generally speaking, the effective focus position calibration portion 373 comprises recorded Z-height (or effective focus position) calibration data. As such, its representation in FIG. 3 as a separate element is intended to be a schematic representation only, and not limiting. In various implementations, the associated recorded Z-height calibration data may be merged with and/or indistinguishable from the lens controller 380, the workpiece focus signal processing portion 375, or a host computer system connected to the system signal and control bus 395, etc.

In various implementations, the exposure time controller 331et controls (e.g., by providing timing signals and/or control signals, etc.) an exposure timing and duration that governs an image exposure of the vision system 300 (e.g., relative to a phase timing of the periodically modulated effective focus position). For example, in an implementation where the light-blocking shutter 365 is included and located along the imaging optical path OPATH between the workpiece 320 and the camera 360, or where the light-blocking shutter 335 is included and located along the illumination path that the source light 332 follows between the light source 330 and the workpiece 320, the exposure time controller 331et may control an exposure timing and duration that governs the operation of the light-blocking shutter 335 or 365 to govern the workpiece image exposure. In various implementations, the light-blocking shutter 235 and/or 265 may comprise a fast optical switch (e.g., a fast liquid crystal optical switch). In other implementations, the exposure time controller 331et may control an exposure timing and duration that governs the operation of an electronic image integration period provided in the camera 360 to govern the workpiece image exposure (e.g., by controlling a fast electronic camera shutter of the camera 360 to acquire an image at a respective controlled time and/or its associated effective focus position). In some implementations, the exposure time controller 331et may be merged with or indistinguishable from the camera 360 and/or the shutter controllers 331sc1 and/or 331sc2.

In various implementations, the exposure time controller 331et may also operate (e.g., during certain modes or timings) to control a strobe timing for the strobe illumination source 330S. For example, such strobed/pulsed lighting operations may be utilized in certain modes (e.g., for points-from-focus operations, etc.), while the quasi-sinusoidal periodic intensity modulated light may be utilized in other modes (e.g., for EDOF operations, etc.). In various implementations, the exposure time controller 331et (e.g., using the Z-height calibration data available in the effective focus position calibration portion 373), may control the strobe illumination source 330S to strobe at a respective controlled time. In one implementation, the exposure time controller 331et may control the strobe illumination source 330S to strobe at a respective phase timing within a period of a standard imaging resonant frequency of the VFL lens 370, so as to acquire an image having a particular effective focus position within the sweeping (periodic modulation) range of the VFL lens 370. Similar timing considerations may also be utilized for the control of other elements by the exposure time controller 331et (e.g., for the control of the light-blocking shutters 335 and/or 365, the camera 360, etc.) It will be appreciated that the operations of the exposure time controller 331et and other features and elements outlined above may generally be implemented to govern workpiece image acquisitions.

In various implementations, a single controller may be configured to provide one or more modulating control signals that are utilized to control the VFL lens 370 to provide the nominally sinusoidal focus position modulation and to control the continuous illumination source 330C to provide the quasi-sinusoidal periodic intensity modulated light. In various implementations, such a single controller may at least one of include or control one or more of the lighting control interface 133, the source driver 333a1 that is configured to drive the continuous illumination source 330C or the lens controller 380. In various implementations, a single controller may provide such modulating control signals based at least in part on the fact that the modulating control signals for the VFL lens 370 and the continuous illumination source 330C may be phase shifted versions of one another, as will be described in more detail below.

Figure 4A:
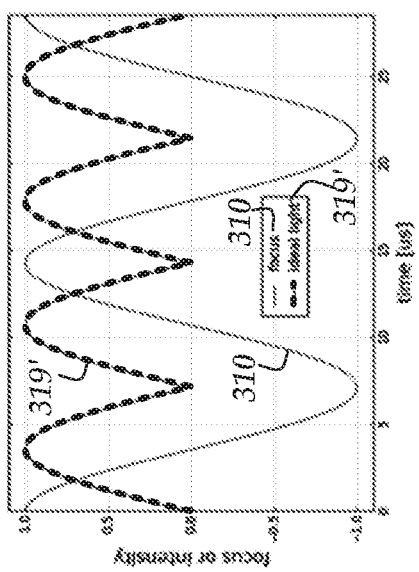
FIGS. 4A-4C are diagrams illustrating an implementation in which a continuous illumination source is driven according to a quasi-sinusoidal periodic drive signal comprising a signal range that includes at least a portion of a full-wave rectified quasi-sinusoidal periodic drive function that repeats at twice the resonant frequency of the TAG lens.
Figure 4B:
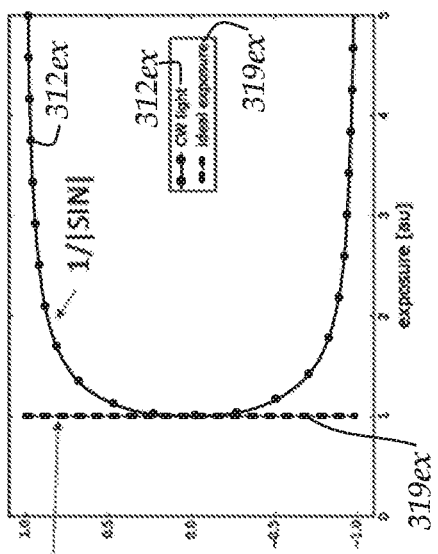
Figure 4C:
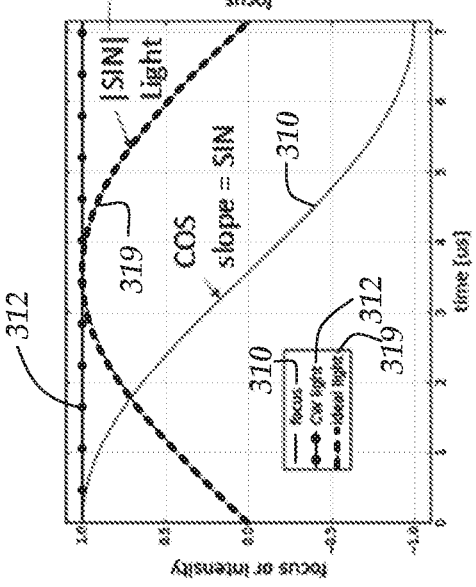

FIGS. 4A-4C are diagrams illustrating an implementation in which a continuous illumination source is driven according to a quasi-sinusoidal periodic drive signal. In FIGS. 4A and 4C, the horizontal axis represents time, and the vertical axis represents focus or intensity (normalized to a maximum value of 1.0), as will be described in more detail below. In FIG. 4B, the horizontal axis represents exposure, and the vertical axis represents focus.

FIG. 4A includes representations of a focus curve 310 and light curves 312 and 319. In various implementations, the focus curve 310 may represent effective focus positions of a vision system (e.g., in accordance with a VFL lens that is controlled to provide a nominally sinusoidal modulation of a focus position of the vision system, as described above with respect to FIGS. 1-3). In the example of FIG. 4A, the focus curve 310 is approximately sinusoidal, as also illustrated in FIG. 4C (i.e., with a longer timeframe), as will be described in more detail below. As shown in FIG. 4A, the light curve 312 corresponds to a constant light source, for which the corresponding intensity is at a constant level (i.e., an intensity of 1.0 on the vertical axis). One issue that can arise in a VFL lens system utilizing such a constant light source is that over-exposure may result at the focus extremes. More specifically, because the focus curve 310 is at least nominally sinusoidal, more time is spent near the extrema of the focus position modulation (e.g., near the 1.0 and −1.0 focus positions) than at the more transitional focuses (e.g., near the 0.0 focus position). As a result, when using a constant light source (e.g., along with an image rate that is significantly slower than the frequency at which the TAG lens is operated), images acquired with a given exposure duration will contain more weighting of the focuses near the extrema (e.g., focuses near the 1.0 and −1.0 focus positions) and less weighting of other focuses (e.g., focuses near the 0.0 focus position). This result is illustrated by a corresponding exposure curve 312ex in FIG. 4B, for which focuses near the extrema (e.g., focuses near the 1.0 and −1.0 focus positions, where the focus position changes slowly as it reverses direction) are shown to have a large normalized exposure level (truncated at a maximum plotted value of 5, but theoretically exceeding that value), while focuses near the more transitional focus levels (e.g., focuses near the 0.0 focus position) have a normalized exposure level of approximately 1.0.

Such varying exposure levels and corresponding weightings, etc. may cause various types of issues. For example, it may generally be undesirable for images to have different exposure levels depending on when the images are acquired during the periodic modulation of the focus position (e.g., as may affect the accuracy of certain types of measurements and/or other processing, etc.). As a specific example with respect to extended depth of field (EDOF) processing, such different exposure levels and/or weightings may be problematic for certain types of de-convolution algorithms that may be used. More specifically, EDOF processing may include image processing that removes defocus blur through deconvolution processing of the workpiece image based on a predetermined integrated point spread function that characterizes operation of the VFL lens system. Such deconvolution processing may assume equal weighting of all focuses, for which the different weightings of the focuses may result in inaccuracies in the image processing.

In accordance with principles disclosed herein, as an alternative to utilizing a constant light source, in various implementations quasi-sinusoidal periodic intensity modulated light may be provided, as described above with respect to FIGS. 1-3. An example of quasi-sinusoidal periodic intensity modulated light is illustrated by the sinusoidal light curve 319 in FIG. 4A. The result of utilizing a light source corresponding to the sinusoidal light curve 319 is represented by the corresponding exposure curve 319ex in FIG. 4B, for which all focus positions are shown to have an exposure level of approximately 1.0. In various implementations, such consistent exposure levels and corresponding weightings of the focus positions throughout the focus range result in more consistent and accurate image processing, measurements, etc.

In various implementations, an exposure at any given focus position may be at least approximately inversely-proportional to the absolute slope of focus vs. time. If the focus curve 310 is designated as a cosine curve, its slope may correspond to a sine curve, for which the exposure may be proportional to 1/|SIN|. In order to normalize the exposure, in accordance with principles disclosed herein, a light source may be utilized for which the intensity may correspond to |SIN|. In one implementation, the intensity of the light source may be represented by an abs(sinusoid), which is 90° out of phase with the nominally sinusoidal modulation of the focus position of the vision system (i.e., as per the operation of the VFL lens). The intensity of such a light source is represented by the light curve 319' of FIG. 4C.

In various implementations, certain types of light sources (e.g., arc lamps, tungsten filaments, etc.) may naturally produce a |SIN| intensity when driven with a SIN current because such light sources luminesce with both a positive and negative current. Certain other types of light sources (e.g., LEDs, etc.) may require a positive current to luminesce, for which the drive current may be rectified (e.g., as corresponding to the light curve 319' of FIG. 4C), or other techniques may be utilized, as will be described in more detail below with respect to FIGS. 5, 6A and 6B. In various implementations, the light curve 319' of FIG. 4C may represent a quasi-sinusoidal periodic drive signal for the light source, as at least approximately corresponding to a full-wave rectified quasi-sinusoidal periodic drive function that repeats at twice the resonant frequency of the TAG lens (i.e., as represented by the focus curve 310). In an alternative implementation, rather than rectifying the negative half-cycles, the light source may be turned off during the negative half-cycles, for which the corresponding representation would include every-other half-cycle of the light curve 319' (e.g., with an intensity value of zero between the positive half-cycles). Such a representation would correspond to a half-wave rectified quasi-sinusoidal periodic drive function that repeats at the resonant frequency of the TAG lens.

Figure 5:
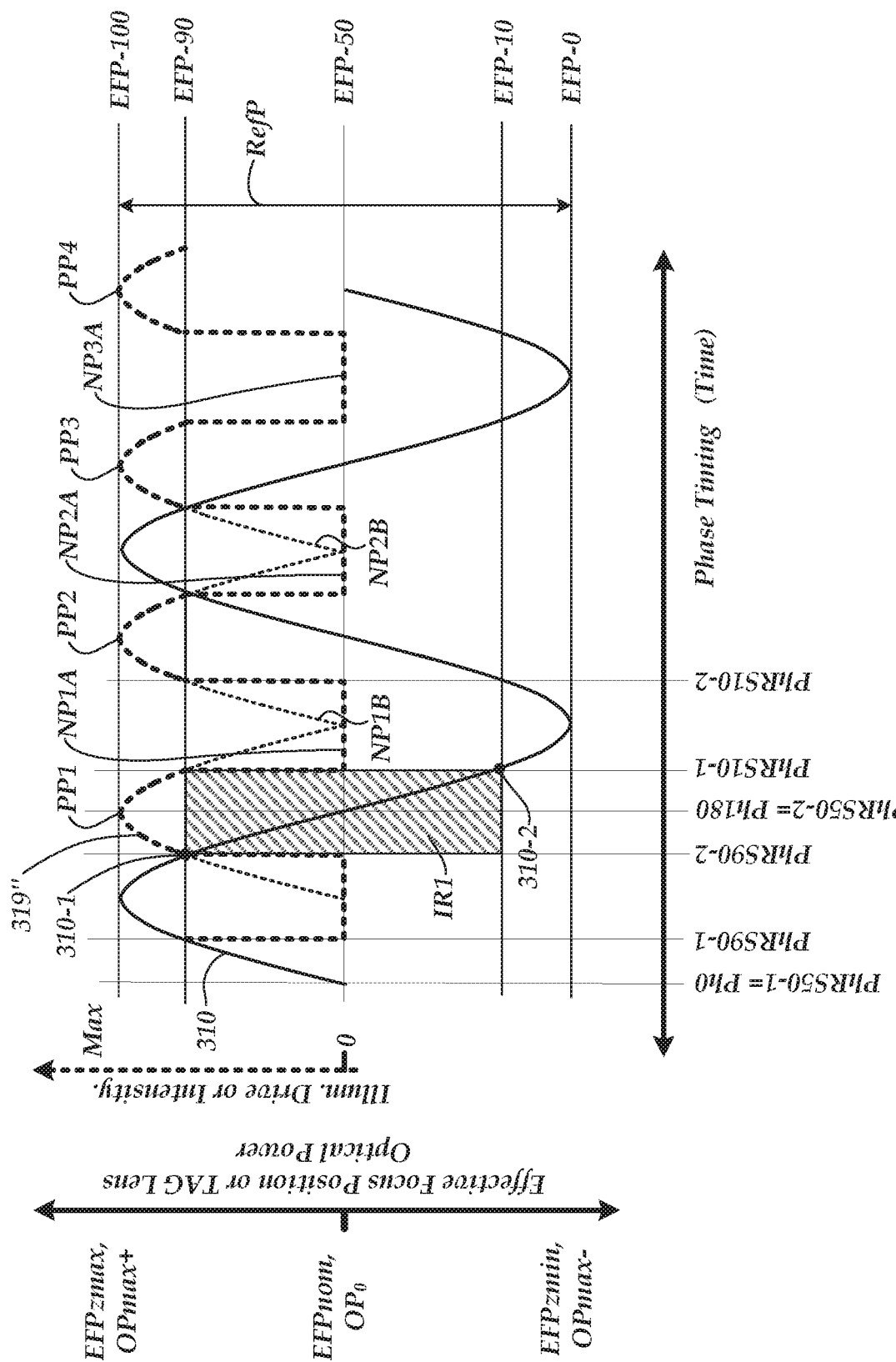
FIG. 5 is a diagram illustrating an implementation similar to that of FIG. 4 wherein the signal range for driving the continuous illumination source includes a peak portion of the full-wave rectified quasi-sinusoidal periodic drive function.
Figure 6:
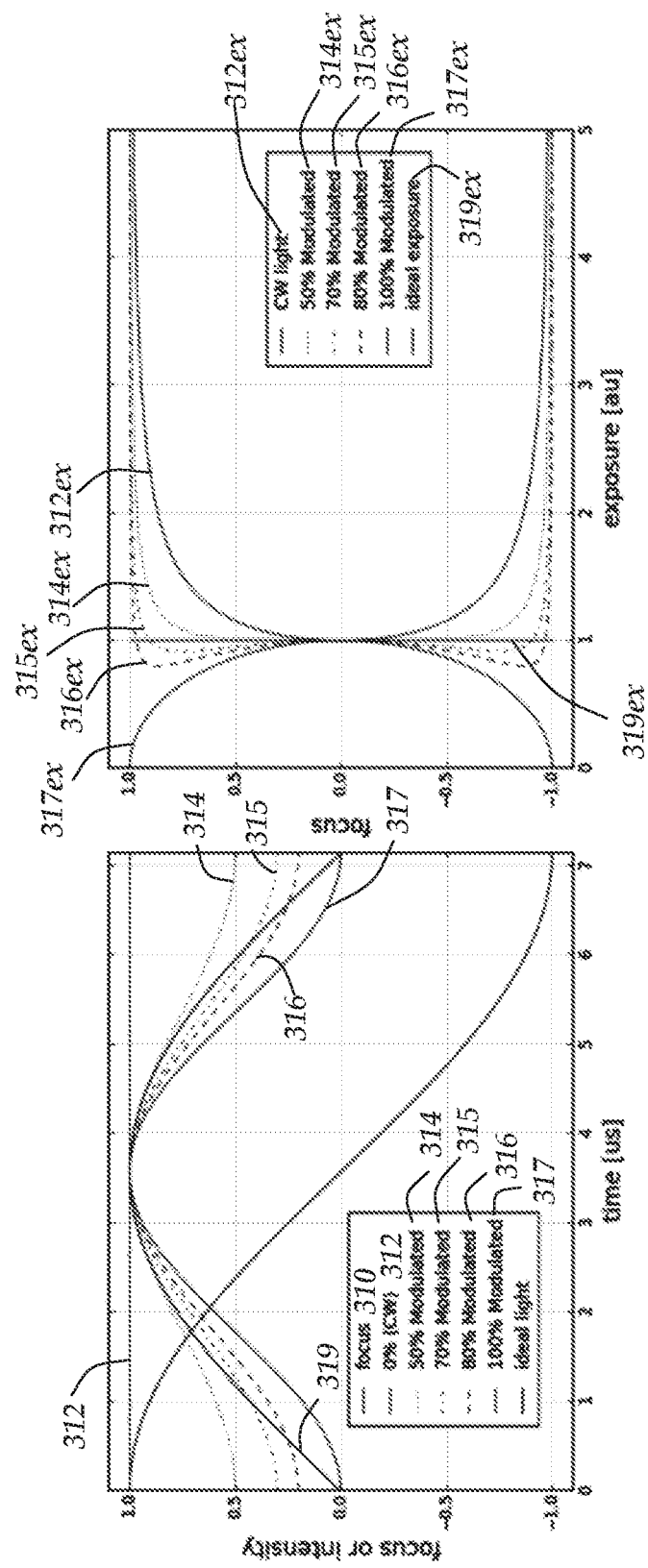
FIGS. 6A-6B are diagrams illustrating an implementation in which a continuous illumination source is driven according to a smoothly varying quasi-sinusoidal periodic drive signal having a frequency that is twice the resonant frequency of the TAG lens and that includes a DC offset component.

FIG. 5 is a diagram illustrating an implementation similar to that of FIG. 4 wherein the signal range for driving the "continuous" illumination source may include a peak portion of the full-wave rectified quasi-sinusoidal periodic drive function. In FIG. 5, the horizontal axis represents time (e.g., phase timing), and the vertical axes represent an effective focus position (as governed by an optical power of the VFL lens), and an illumination drive signal or intensity, respectively. It will be understood that the effective focus position EFP in front of the objective lens (e.g., the lens 350) during an image exposure corresponds to the optical power of the VFL lens during that image exposure. It will be appreciated that imperfections in any particular VFL lens system may contribute to various non-linearities or distortions in the relationship between the two vertical axes, but the general nominal relationship is illustrated.

FIG. 5 includes representations of the focus curve 310 and a light curve 319". The light curve 319" may include certain characteristics similar to those of the light curve 319' of FIG. 4C, except as otherwise described below. Effective focus positions (EFP) of the vision system with respect to the focus curve 310 are indicated on the right-hand side of FIG. 5. The focus range Refp of the vision system is indicated as varying between an effective focus position of EFP-0 and an effective focus position of EFP-100 (e.g., corresponding to the range of focus values from −1.0 to 1.0 in FIGS. 4A-4C and 6A-6B). In this particular example, the effective focus position EFP-50 (e.g., corresponding to a focus value of 0.0 in FIGS. 4A-4C and 6A-6B) is an example of a nominal focus position EFP-nom, which is designated to be a nominal focus position (e.g., wherein the optical power of the VFL lens 370 is zero). According to this description, EFP-nom may approximately correspond to the nominal focal length of the objective lens (e.g., objective lens 350) in some implementations. Thus, EFP-nom (e.g., EFP-50) may be in the middle of the focus range Refp which varies from EFP-0 to EFP-100.

The focus curve 310 is shown to have values at the effective focus position EFP-50 at phase timings PhRS50-1 and PhRS50-2 (corresponding to phase timing values of Ph0=0 degrees and Ph180=180 degrees, respectively). Values at the effective focus position EFP-90 occur at the phase timings PhRS90-1 and PhRS90-2, and values at the effective focus position EFP-10 occur at the phase timings PhRS10-1 and PhRS10-2. As will be described in more detail below, the portion of the focus curve 310 between the effective focus positions EFP-10 and EFP-90 (i.e., the portion of the focus curve 310 between the points 310-1 and 310-2) represents 80% of the focus range Refp (i.e., with the total focus range Refp being from the effective focus position EFP-0 to the effective focus position EFP-100). It will be understood that the explicitly designated phase timings may be representative of other phase timings relative to the periodic modulation of the VFL lens (e.g., the VFL lens 370), which may be represented along the horizontal axis and may correspondingly repeat for each subsequent periods of the focus curve 310.

As will be described in more detail below, in various implementations the operational focus range of the VFL lens system may be restricted for various reasons (e.g., by elements of the control system portion 120, or otherwise) to be less than the full focus range (e.g., the focus range Refp of FIG. 5). That is, the extrema (e.g., the positive and negative peaks) of the nominally sinusoidal focus position modulation may be excluded from a desirable operating focus range to be used for imaging and/or measurement. In one implementation, the operational focus range may correspond to a specified percentage (e.g., 80% or less) of the full focus range provided by the operation of the VFL lens. In such implementations, if desired, the continuous illumination may be at least one of interrupted or turned off for at least a part of the full focus range that is outside of the operational focus range of the VFL lens system.

As one specific illustrative example, in one implementation the operational focus range of the VFL lens system may be made to correspond to 80% of the full focus range (e.g., including the focus range between the effective focus positions of EFP-10 and EFP-90). In such an implementation, the light curve 319", which might otherwise include a non-peak portion NP1B (e.g., similar to the light curve 319' of FIG. 4C), may instead correspond to the light source being turned-off or interrupted (e.g., as indicated by the alternatively illustrated non-peak portion NP1A). In accordance with such an implementation, the peak portion PP1 of the light curve 319" (i.e., occurring between the phase timings PhRS90-2 and PhRS10-1) may correspond to an illustrated "illumination range" IR1. In the illumination range IR1, the quasi-sinusoidal periodic intensity modulated light is provided over the corresponding portion of the operational focus range (e.g., including the corresponding portion of the focus curve 310 between the points 310-1 and 310-2), and the light source may be turned off at other times, in some implementations, as illustrated. It will be appreciated that in other implementations, the light source intensity may simply be held constant at a desired level, or reduced to follow a "low intensity" portion of a drive function if desired, rather than completely turning off the light source (e.g., to avoid start up latency issues that might occur in some light sources or drive circuits.)

In one implementation corresponding to FIG. 5, a source driver may be configured to drive the continuous illumination source according to a quasi-sinusoidal periodic drive signal comprising a signal range that includes at least a peak portion of a full-wave rectified quasi-sinusoidal periodic drive function that repeats at twice the resonant frequency of the VFL (TAG) lens. That is, the peak portions of the full-wave rectified quasi-sinusoidal periodic drive function repeat at twice the resonant frequency of the VFL (TAG) lens, during both polarities of focus change within the resonant period. In such an implementation, the light curve 319" may be represented as including the peak portions PP1-PP4, and the non-peak portions NP1A-NP3A. In an alternative implementation, a source driver may be configured to drive the continuous illumination source according to a quasi-sinusoidal periodic drive signal comprising a signal range that includes at least a peak portion of a half-wave rectified quasi-sinusoidal periodic drive signal function that repeats at the resonant frequency of the VFL (TAG) lens. In such an implementation, the light curve 319" may be represented as including the peak portions PP1 and PP3, with the non-peak portions NP1A-NP3A and similar non-peak portions replacing the peak portions PP2 and PP4.

In various implementations, an image exposure may be made to include at least two exposure increments corresponding to a same focus position and acquired during different periods of the nominally sinusoidal focus position modulation. For example, a first exposure increment may correspond to the effective focus position EFP-90 at the start of the peak portion PP1 (i.e., corresponding to the phase timing PhRS90-2) during a first period of the nominally sinusoidal focus position modulation represented by the focus curve 310, and a second exposure increment may correspond to the effective focus position EFP-90 at the start of the peak portion PP3 during a second period of the nominally sinusoidal focus position modulation represented by the focus curve 310.

FIGS. 6A-6B are diagrams illustrating an implementation in which the continuous illumination source may be driven according to a smoothly varying quasi-sinusoidal periodic drive signal having a frequency that is twice the resonant frequency of the TAG lens and that includes a DC offset component. In FIG. 6A, the horizontal axis represents time, and the vertical axis represents focus or intensity, and in FIG. 6B, the horizontal axis represents exposure, and the vertical axis represents focus. FIGS. 6A-6B have certain similarities to FIGS. 4A-4C, and relative to the light curve 319' of FIG. 4C, certain light curves in FIG. 6A represent an alternative in which rather than driving the light source with a |SIN| function, the |SIN| wave is essentially approximated with an offset COS wave at twice the TAG frequency.

FIG. 6A includes representations of the focus curve 310 and the light curves 312 and 319, which are similar to those illustrated in FIG. 4A. FIG. 6A also illustrates additional light curves 314-317, which are representative of different modulation levels for which the continuous illumination source may be driven according to a smoothly varying quasi-sinusoidal periodic drive signal having a frequency that is twice the resonant frequency of the TAG lens. In various implementations, the light curve 312 may correspond to a 0% modulation, the light curve 314 may correspond to a 50% modulation, the light curve 315 may correspond to a 70% modulation, the light curve 316 may correspond to an 80% modulation and the light curve 317 may correspond to a 100% modulation. In various implementations, the light curve 314 may have a DC offset corresponding approximately to the 0.75 level on the vertical axis and an amplitude that ranges between 0.5 and 1.0. The light curve 315 may have a DC offset corresponding approximately to the 0.65 level on the vertical axis and an amplitude that ranges between 0.3 and 1.0, and the light curve 316 may have a DC offset corresponding approximately to the 0.60 level on the vertical axis and an amplitude that ranges between 0.2 and 1.0. In various implementations, a quasi-sinusoidal periodic intensity modulated light as defined herein may correspond to any of the light curves 314-319 of FIG. 6A as well as the light curve 319' of FIG. 4C or the various implementations of the light curve 319" of FIG. 5, or any other light curves with similar or other quasi-sinusoidal characteristics.

FIG. 6B includes exposure curves 312ex-319ex as corresponding to the light curves 312-319 of FIG. 6A. The exposure curves 312ex and 319ex (corresponding to the light curves 312 and 319) are similar to those illustrated in FIG. 4B. As noted above with respect to FIG. 4B, one issue with the exposure curve 312ex is that focuses near the extrema (e.g., focuses near the 1.0 and −1.0 focus positions) are shown to have an exposure level approaching a value of 5, while focuses near the more transitional focus levels (e.g., focuses near the 0.0 focus position) have an exposure level of approximately 1.0. The exposure curves 314ex-316ex are shown to achieve various improvements in this regard, in that greater portions of the exposure curves are closer to the exposure level of 1.0, as contrasted with the exposure curve 312ex. In comparing the exposure curves 314ex-316ex to one another, the exposure curve 314ex includes more portions to the right of the ideal exposure curve 319ex, while the exposure curve 316ex includes more portions to the left of the ideal exposure curve 319ex, with the exposure curve 315ex located between the exposure curves 314ex and 316ex. In various implementations, a light curve corresponding to an exposure curve between the exposure curves 314ex and 316ex (i.e., between 50% and 80% modulation) may be utilized to approximate the ideal exposure curve 319ex.

In various implementations in which a modulated light curve similar to those FIG. 6A is to be utilized, as noted above, the source driver (e.g., quasi-sine source driver 333a1 of FIG. 3) may be configured to drive the continuous illumination source according to a smoothly varying quasi-sinusoidal periodic drive signal having a frequency that is twice the resonant frequency of the TAG lens and that includes a DC offset component. In various implementations, the smoothly varying quasi-sinusoidal periodic drive signal may correspond to a function of time DS(t) which at least approximately corresponds to the equation:

$$DS(t)=K^*[(1-0.5^*MC)-(0.5^*MC)^*\cos(2\omega_{TAG}^*t)]\qquad\text{Eq. 1}$$

wherein MC represents a modulation coefficient that is at least 0.3 and at most 1.0, $\omega_{TAG}$ represents the resonant frequency of the TAG lens, t represents time, and K is a constant representing the maximum value of DS(t). In various implementations, MC may be at least 0.5 and at most 0.8 (e.g., corresponding to a value between the 50% and 80% modulation as described above).

In general with respect to the configurations of FIGS. 1-6, in various implementations the nominally sinusoidal focus position modulation may correspond to a focus position modulation F(t) as a function of time (t), which has a rate of change dF(t)/dt as a function of time (t). The source driver may be configured to drive the continuous illumination source to provide quasi-sinusoidal periodic intensity modulated light having an intensity that corresponds to an intensity modulation I(t) as a function of time (t), that, at least throughout the operational focus range of the VFL lens system, satisfies the condition:

$$0.9\ RE<I(t)/\text{ABS}(dF(t)/dt)<1.1\ RE\qquad\text{Eq. 2}$$

wherein ABS(dF(t)/dt) represents the absolute value of the rate of change of focus at a time (t), and RE represents a constant rate of exposure per increment of focus change.

It will be appreciated that the configurations described above may provide various advantages. For example, in various implementations, a vision system in accordance with the principles disclosed herein may utilize a continuous light source that is less complex and/or less expensive than that required by certain other vision systems (e.g., utilizing a pulsed or strobed light source for certain applications). More specifically, in certain implementations a continuous light source 330C may be utilized which has a relatively slower response time. In contrast, illumination and/or exposure using certain pulsed light source configurations may have relatively faster response times (e.g., low latency light pulses of approximately 10 ns, or ≈100 MHz) for which a more complex and expensive light source may be required. In addition, more light may be provided for imaging and/or exposing a workpiece utilizing configurations such as those disclosed herein, for which the |SIN| RMS light intensity may be on the order of 65-70% of the light provided by a constant light source configuration. In contrast, for a pulsed light configuration, the total integrated light may be significantly lower. Thus, the continuous light source 330C when operated as disclosed herein, may be utilized to image workpiece features (e.g., in darker areas), including when magnifications are relatively high, operate with shorter exposure durations with less power required, and may be able to achieve less image noise.

Figure 7:
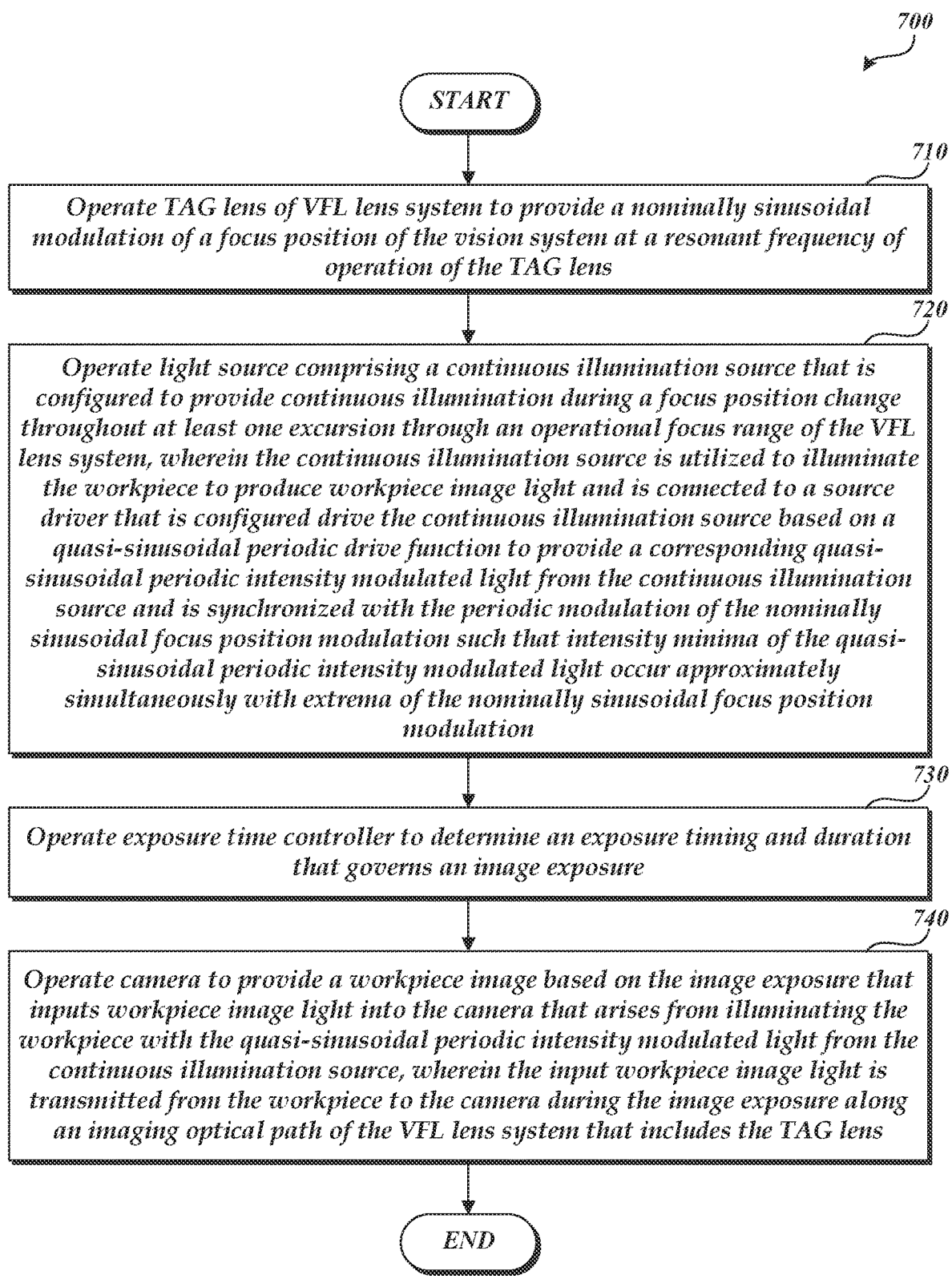
FIG. 7 is a flow diagram illustrating one exemplary implementation of a routine for operating a vision system including a continuous illumination source that is driven based on a quasi-sinusoidal periodic drive function according to principles disclosed herein.

FIG. 7 is a flow diagram illustrating one exemplary implementation of a routine 700 for operating a vision system including a continuous illumination source that is driven based on a quasi-sinusoidal periodic drive function according to principles disclosed herein. At a block 710, a variable focal length tunable acoustic gradient index of refraction (TAG) lens of a variable focal length (VFL) lens system is operated to provide a nominally sinusoidal modulation of a focus position of the vision system at a resonant frequency of operation of the TAG lens. At a block 720, a light source is operated comprising a continuous illumination source that is configured to provide continuous illumination during a focus position change throughout at least one excursion through an operational focus range of the VFL lens system. The continuous illumination source is utilized to illuminate the workpiece to produce workpiece image light and is connected to a source driver that is configured drive the continuous illumination source based on a quasi-sinusoidal periodic drive function to provide a corresponding quasi-sinusoidal periodic intensity modulated light from the continuous illumination source. The source driver is synchronized with the periodic modulation of the nominally sinusoidal focus position modulation such that intensity minima of the quasi-sinusoidal periodic intensity modulated light occur approximately simultaneously with extrema of the nominally sinusoidal focus position modulation.

At a block 730, an exposure time controller is operated to determine an exposure timing and duration that governs an image exposure. At a block 740, a camera is operated to provide a workpiece image based on the image exposure that inputs workpiece image light into the camera that arises from illuminating the workpiece with the quasi-sinusoidal periodic intensity modulated light from the continuous illumination source. The input workpiece image light is transmitted from the workpiece to the camera during the image exposure along an imaging optical path of the VFL lens system that includes the TAG lens.

In various implementations, various types of image processing may be performed on the workpiece image. For example, in a configuration in which the image that is acquired is an EDOF image, image processing may be performed to remove defocus blur, which may include deconvolution processing of the workpiece image (e.g., based on a predetermined integrated point spread function that characterizes operation of the VFL lens system, etc.) As described above, such deconvolution processing may be able to be performed more accurately on an EDOF image that is obtained utilizing the quasi-sinusoidal periodic intensity modulated light as disclosed herein (e.g., as opposed to utilization of a constant light source which may result in different weightings of different focuses in the EDOF image which may result in inaccuracies in the deconvolution processing).

While preferred implementations of the present disclosure have been illustrated and described, numerous variations in the illustrated and described arrangements of features and sequences of operations will be apparent to one skilled in the art based on this disclosure. Various alternative forms may be used to implement the principles disclosed herein. In addition, the various implementations described above can be combined to provide further implementations. All of the U.S. patents and U.S. patent applications referred to in this specification are incorporated herein by reference, in their entirety. Aspects of the implementations can be modified, if necessary to employ concepts of the various patents and applications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled.

The invention claimed is:

1. A vision system for providing an image of a workpiece, the vision system comprising:
   a variable focal length (VFL) lens system including a variable focal length tunable acoustic gradient index of refraction (TAG) lens that is controlled to provide a nominally sinusoidal modulation of a focus position of the vision system at a resonant frequency of operation of the TAG lens;
   a light source comprising a continuous illumination source that is configured to provide continuous illumination during a focus position change throughout at least one excursion through an operational focus range of the VFL lens system, and that may be utilized to illuminate the workpiece to produce workpiece image light, wherein the continuous illumination source is connected to a source driver that is configured to drive the continuous illumination source based on a quasi-sinusoidal periodic drive function to provide a corresponding quasi-sinusoidal periodic intensity modulated light from the continuous illumination source and is synchronized with a periodic modulation of the nominally sinusoidal focus position modulation such that intensity minima of the quasi-sinusoidal periodic intensity modulated light occur approximately simultaneously with extrema of the nominally sinusoidal focus position modulation;
   an exposure time controller that is configured to determine an exposure timing and duration that governs an image exposure; and
   a camera configured to provide a workpiece image based on the image exposure that inputs workpiece image light into the camera that arises from illuminating the workpiece with the quasi-sinusoidal periodic intensity modulated light from the continuous illumination source, wherein the input workpiece image light is transmitted from the workpiece to the camera during the image exposure along an imaging optical path of the VFL lens system that includes the TAG lens.

2. The vision system of claim 1, wherein the exposure time controller is configured to determine an exposure timing and duration that governs operation of an electronic image integration period provided in the camera to govern the workpiece image exposure.

3. The vision system of claim 1, further comprising a light-blocking shutter located along one of the imaging optical path between the workpiece and the camera, or an illumination path between the light source and the workpiece, wherein the exposure time controller is configured to determine an exposure timing and duration that governs operation of the light-blocking shutter to govern the workpiece image exposure.

4. The vision system of claim 3, wherein the light-blocking shutter is located along the illumination path.

5. The vision system of claim 3, wherein the light-blocking shutter comprises a fast optical switch.

6. The vision system of claim 5, wherein the fast optical switch comprises a fast liquid crystal optical switch.

7. The vision system of claim 1, wherein the operational focus range of the VFL lens system corresponds to 80% or less of a full focus range provided by the operation of the TAG lens.

8. The vision system of claim 7, wherein the continuous illumination is provided over the full focus range provided by the operation of the TAG lens.

9. The vision system of claim 7, wherein the continuous illumination is at least one of interrupted or turned off for at least a part of the full focus range that is outside of the operational focus range of the VFL lens system.

10. The vision system of claim 1, wherein the source driver is configured to drive the continuous illumination source according to a quasi-sinusoidal periodic drive signal comprising a signal range that includes at least a peak portion of a half-wave rectified quasi-sinusoidal periodic drive signal function that repeats at the resonant frequency of the TAG lens, or a signal range that includes at least a peak portion of a full-wave rectified quasi-sinusoidal periodic drive function that repeats at twice the resonant frequency of the TAG lens.

11. The vision system of claim 10, wherein the quasi-sinusoidal periodic drive signal comprises a signal range that includes at least the peak portion of the half-wave rectified quasi-sinusoidal periodic drive function that repeats at the resonant frequency of the TAG lens.

12. The vision system of claim 10, wherein the quasi-sinusoidal periodic drive signal comprises a signal range that includes at least the peak portion of the full-wave rectified quasi-sinusoidal periodic drive function that repeats at twice the resonant frequency of the TAG lens.

13. The vision system of claim 1, wherein the source driver is configured to drive the continuous illumination source according to a smoothly varying quasi-sinusoidal periodic drive signal having a frequency that is twice the resonant frequency of the TAG lens and that includes a DC offset component.

14. The vision system of claim 13, wherein the smoothly varying quasi-sinusoidal periodic drive signal is a function of time DS(t) which at least approximately corresponds to the equation:

$$DS(t)=K*[(1-0.5* MC)-(0.5*MC)*\cos(2\omega_{TAG}*t)]$$

wherein MC represents a modulation coefficient that is at least 0.3 and at most 1.0, $\omega_{TAG}$ represents the resonant frequency of the TAG lens, t represents time, and K is a constant representing the maximum value of DS(t).

15. The vision system of claim 14, wherein MC is at least 0.5 and at most 0.8.

16. The vision system of claim 1, wherein the nominally sinusoidal focus position modulation corresponds to a focus position modulation F(t) as a function of time (t), which has a rate of change dF(t)/dt as a function of time (t), and the source driver is configured to drive the continuous illumination source to provide quasi-sinusoidal periodic intensity modulated light having an intensity that corresponds to an intensity modulation I(t) as a function of time (t), that, at least throughout the operational focus range of the VFL lens system, satisfies the condition:

$$0.9\ RE<I(t)/ABS(dF(t)/dt)<1.1\ RE$$

wherein ABS(dF(t)/dt) represents the absolute value of the rate of change of focus at a time (t), and RE represents a constant rate of exposure per increment of focus change.

17. The vision system of claim 1, wherein the image exposure comprises at least two exposure increments corresponding to the same focus position and acquired during different periods of the nominally sinusoidal focus position modulation.

18. The vision system of claim 1, wherein a single controller is configured to provide one or more modulating control signals that are utilized to control the TAG lens to provide the nominally sinusoidal focus position modulation and to control the continuous illumination source to provide the quasi-sinusoidal periodic intensity modulated light.

19. The vision system of claim 18, wherein the single controller at least one of comprises or controls the source driver that is configured to drive the continuous illumination source.

20. A method for operating a vision system, the method comprising:
operating a variable focal length tunable acoustic gradient index of refraction (TAG) lens of a variable focal length (VFL) lens system to provide a nominally sinusoidal modulation of a focus position of the vision system at a resonant frequency of operation of the TAG lens;
operating a light source comprising a continuous illumination source that is configured to provide continuous illumination during a focus position change throughout at least one excursion through an operational focus range of the VFL lens system, wherein the continuous illumination source is utilized to illuminate a workpiece to produce workpiece image light and is connected to a source driver that is configured to drive the continuous illumination source based on a quasi-sinusoidal periodic drive function to provide a corresponding quasi-sinusoidal periodic intensity modulated light from the continuous illumination source and is synchronized with a periodic modulation of the nominally sinusoidal focus position modulation such that intensity minima of the quasi-sinusoidal periodic intensity modulated light occur approximately simultaneously with extrema of the nominally sinusoidal focus position modulation;
operating an exposure time controller to determine an exposure timing and duration that governs an image exposure; and
operating a camera to provide a workpiece image based on the image exposure that inputs workpiece image light into the camera that arises from illuminating the workpiece with the quasi-sinusoidal periodic intensity modulated light from the continuous illumination source, wherein the input workpiece image light is transmitted from the workpiece to the camera during the image exposure along an imaging optical path of the VFL lens system that includes the TAG lens.

21. The method of claim 20, further comprising performing image processing on the workpiece image.

22. The method of claim 21, wherein the image processing removes defocus blur and comprises deconvolution processing of the workpiece image based on a predetermined integrated point spread function that characterizes the operation of the VFL lens system.

23. A vision system, comprising:
a variable focal length (VFL) lens system including a variable focal length tunable acoustic gradient index of refraction (TAG) lens;
a light source comprising a continuous illumination source;
a camera; and
a control system, comprising:
one or more processors; and
a memory coupled to the one or more processors and storing program instructions that when executed by the one or more processors cause the one or more processors to at least:
control the TAG lens to provide a nominally sinusoidal modulation of a focus position of the vision system at a resonant frequency of operation of the TAG lens;
control the continuous illumination source to provide continuous illumination during a focus position change throughout at least one excursion through an operational focus range of the VFL lens system, wherein the continuous illumination source is utilized to illuminate a workpiece to produce workpiece image light and is driven based on a quasi-sinusoidal periodic drive function to provide a corresponding quasi-sinusoidal periodic intensity modulated light from the continuous illumination source and is synchronized with a periodic modulation of the nominally sinusoidal focus position modulation such that intensity minima of the quasi-sinusoidal periodic intensity modulated light occur approximately simultaneously with extrema of the nominally sinusoidal focus position modulation; and
control the camera to provide a workpiece image based on an image exposure that inputs workpiece image light into the camera that arises from illuminating the workpiece with the quasi-sinusoidal periodic intensity modulated light from the continuous illumination source, wherein the input workpiece image light is transmitted from the workpiece to the camera during the image exposure along an imaging optical path of the VFL lens system that includes the TAG lens.

* * * * *